United States Patent [19]

Archibald et al.

[11] Patent Number: 4,694,012

[45] Date of Patent: Sep. 15, 1987

[54] METHOD OF TREATING OF PREVENTING DISEASES USING 1,4-DIHYDROPYRIDINES

[75] Inventors: John L. Archibald, Farnham Royal; Terence J. Ward; Albert Opalko, both of Maidenhead, all of England

[73] Assignee: John Wyeth & Brother Limited, Maidenhead, England

[21] Appl. No.: 760,705

[22] Filed: Jul. 30, 1985

[30] Foreign Application Priority Data

Aug. 17, 1984 [GB] United Kingdom ............... 8421039

[51] Int. Cl.$^4$ ............................................. A61K 31/44
[52] U.S. Cl. .................................. 514/332; 514/341; 514/356
[58] Field of Search ................ 514/332, 333, 356, 341

[56] References Cited

U.S. PATENT DOCUMENTS

| 4,154,822 | 5/1979 | Polimeni et al. | 514/54 |
| 4,430,333 | 2/1984 | Campbell et al. | 514/356 |
| 4,572,909 | 2/1986 | Campbell et al. | 514/356 |
| 4,590,195 | 5/1986 | Alker | 514/333 |

FOREIGN PATENT DOCUMENTS

| 0060674 | 9/1982 | European Pat. Off. | 514/356 |
| 100189 | 2/1984 | European Pat. Off. | |

Primary Examiner—Leonard Schenkman
Assistant Examiner—Joseph A. Lipovsky
Attorney, Agent, or Firm—Arthur G. Seifert

[57] ABSTRACT

This invention concerns a method of treatment using 1,4-dihydropyridine derivatives having the formula

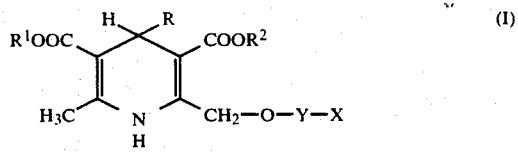

or a pharmaceutically acceptable salt thereof, wherein
R is aryl or heteroaryl;
$R^1$ and $R^2$ are each independently $C_1$-$C_4$ alkyl or 2-methoxyethyl;
Y is —$(CH_2)_n$—, —$CH_2CH(CH_3)$— or —$CH_2C(CH_3)_2$—;
X is a 5 or 6 membered nitrogen containing aromatic heterocyclic ring which may optionally be substituted by one or more $C_1$-$C_4$ alkyl, phenyl, benzyl, CN, —$N(R^3)_2$, $(CH_2)_mCO_2H$, $(CH_2)_mCO_2(C_1$-$C_4$ alkyl) or $(CH_2)_mCON(R^3)_2$ groups wherein each $R^3$ is independently H or $C_1$-$C_4$ alkyl and m is 0 or 1;
and n is 1 to 3 when X is linked by a ring carbon atom or 2 or 3 when X is linked by a ring nitrogen atom.

11 Claims, No Drawings

METHOD OF TREATING OF PREVENTING DISEASES USING 1,4-DIHYDROPYRIDINES

This invention relates to a method of treatment using 1,4-dihydropyridine derivatives, more particularly to a method for the treatment or prevention of diseases responsive to the inhibition of blood platelet aggregation and/or inhibition of the enzymes thromboxane synthetase and/or phospholipase.

In European Patent Publication No. 100189 there are disclosed compounds having the formula

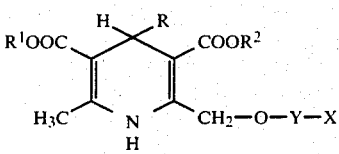

wherein
R is aryl or heteroaryl;
$R^1$ and $R^2$ are each independently $C_1$–$C_4$ alkyl or 2-methoxyethyl;
Y is —$(CH_2)_n$—, —$CH_2CH(CH_3)$— or —$CH_2C(CH_3)_2$—;
X is a 5 or 6 membered nitrogen containing aromatic heterocyclic ring which may optionally be substituted by one or more $C_1$–$C_4$ alkyl, phenyl, benzyl, CN, —$N(R^3)_2$, $(CH_2)_mCO_2H$, $(CH_2)_mCO_2(C_1$–$C_4$ alkyl) or $(CH_2)_mCON(R^3)_2$ groups wherein each $R^3$ is independently H or $C_1$–$C_4$ alkyl and m is 0 or 1;
and n is 1 to 3 when X is linked by a ring carbon atom or 2 or 3 when X is linked by a ring nitrogen atom; which compounds are stated to possess antihypertensive and anti-ischaemic properties.

We have now surprisingly found that compounds of formula I possess both blood platelet and thromboxane synthetase - inhibitory properties and hence may be used in the treatment or prevention of diseases responsive to such properties such as thrombosis, atherosclerosis, peripheral vascular diseases and migraine.

Accordingly in one aspect this invention provides a method for treating or preventing disorders responsive to inhibition of blood platelet aggregation or thromboxane synthetase in a mammal which comprises administering to said mammal an effective amount of a compound of formula I as shown above or a pharmaceutically acceptable salt thereof.

This invention also provides use of a compound of formula I as shown above or a pharmaceutically acceptable salt thereof in the preparation of a medicament for the treatment or prevention of disorders responsive to inhibition of blood platelet aggregation or thromboxane synthetase, e.g. thrombosis, atherosclerosis, peripheral vascular disease or migraine.

Examples of the groups R, $R^1$, $R^2$ X and Y in formula I are given in EP No. 100189.

In the methods of this invention preferred examples of R are optionally substituted phenyl such as halophenyl (e.g. 2-chlorophenyl, pentafluorophenyl); dihalophenyl (e.g. 2,3-dichlorophenyl); nitrophenyl (e.g. 2- or 3-nitrophenyl); trifluoromethylphenyl; (e.g. 2-trifluoromethylphenyl).

Examples of $R^1$ and/or $R^2$ are methyl, ethyl, n-propyl, isopropyl, n-butyl and t-butyl.

Examples of X are imidazo.lyl,(e.g. 1-imidazolyl) and pyridyl (e.g. 3-pyridyl).

Examples of Y are —$CH_2$—and —$CH_2CH_2$—.

Compounds of formula I were tested for their ability to inhibit blood platelet aggregation by a modification of the procedure of Fantl, Australian J. Exp. Biol. Med. Sci. 45, 355-62 1967.

Since platelet aggregation is the initial step in thrombus formation it is considered that compounds which prevent aggregation or reduce platelet adhesiveness may inhibit the initiation of the atherosclerotic process. The effect of drugs on aggregation is measured in platelet-rich plasma containing a small amount of arachidonic acid which markedly increases aggregation in vitro and may be a physiological agent for doing so in vivo. The actual test procedure used is described below.

New Zealand White rabbits (2.5–3kg) are anaesthetised with an injection, via the marginal ear vein, of sodium pentobarbitone 30–40 mg/kg. The carotid artery is cannulated and blood (100–150 ml) is withdrawn into 50 ml syringes containing 3.8% sodium citrate (Ratio blood: citrate =9:1).

Blood is centrifuged at 200g (1500 r.p.m.) for 10 minutes at 5° C. and the platelet rich plasma (PRP) removed. The platelets are then kept at room temperature in a screw topped plastic centrifuge tube for the duration of the experiment.

A twin channel platelet aggregometer—(HU aggregometer, A. Browne Ltd, Leicester, UK) is used. 1.0 ml aliquots of PRP are prewarmed for 5–10 minutes and stirred continuously at 1100 rpm. Aggregation is induced by addition of 250μM arachidonic acid, (8 μl volume) to the PRP samples. The aggregometer output is set at maximum and the chart recorder sensitivity is altered to give a full scale deflection to this arachidonic acid response.

Control responses are recorded as the maximum deflection obtained after addition of 250μM arachidonic acid.

PRP samples are preincubated for 1 minute with the test compounds followed by arachidonic acid addition. The maximum deflection after the addition of arachidonic acid is then recorded. All drugs are screened initially at $10^{-4}$M (final concentration), i.e. 10 μl of a $1\times10^{-2}$M stock solution of the drug dissolved in distilled water is added to the PRP.

Dazoxiben, a thromboxane synthetase inhibitor (Randall, M. J. et al Research 23 145-162, 1981) is used as a positive control and all test components are compared with Dazoxiben. The activity of the test compound is expressed as the ratio $IC_{50}$ Dazoxiben/$IC_{50}$ Test where $IC_{50}$ is the dose required to inhibit the A.A. induced aggregation by 50%. The greater the ratio the more potent the compound to Dazoxiben.

| COMPOUND | Inhibition of blood platelet aggregation potency ratio (dazoxiben = 1) |
|---|---|
| 1,4-Dihydro-2-methyl-4-(2-nitrophenyl)-6-[(3-pyridylmethoxy)methyl]pyridine-3,5-dicarboxylic acid diethyl ester | 0.65 |
| 1,4-Dihydro-2-methyl-4-(3-nitrophenyl)-6-[(3-pyridylmethoxy)methyl]pyridine-3,5-dicarboxylic acid 5-ethyl 3-methyl diester | 0.65 |
| 1,4-Dihydro-2-methyl-4-(3-nitrophenyl)-6-[(3-pyridylethoxy)methylpyridine-3,5-dicarboxylic acid 5-ethyl-3-methyl diester | 1.68 |

Compounds possessing thromboxane synthetase inhibitory activity are useful in the treatment or prevention of diseases responsive to the inhibition of thromboxane synthetase especially cardiovascular disorders such as thrombosis, atherosclerosis, cerebral ischaemic attacks; and angina pectoris; peripheral vascular diseases and migraine.

The compounds of formula I were tested for their ability to inhibit thromboxane production by the following standard test:

(a) Generation of thromboxanes

Blood (approx. 75 ml) is obtained from an anaesthetised rabbit and centrifuged at 200g for 10 minutes to obtain platelet rich plasma (PRP). An aliquot of PRP is incubated for 10 minutes to obtain platelet rich plasma (PRP). An aliquot of PRP is incubated for 10 minutes at 37° C. in the presence of vehicle or drug. Platelet aggregation is induced by the addition of adenosine diphosphate and adrenalin. The tubes are incubated for 3 minutes, centrifuged at 10,000 for 3 minutes and a 50 ml aliquot of the supernatant taken for radio-immunoassay of thromboxane $B_2$ ($TxB_2$).

(b) Radio-immunoassay of $TxB_2$

The total incubation volume is 150μ containing 50μl of $3_H$—$TxB_2$ (0.005 μCi), 50 ml of sample or authentic $TxB_2$ ranging from 5 to 300 pg per tube as standards and 50μl of rabbit anti-sera to $TxB_2$ (in a concentration which will bind 50% of H-$TxB_2$). After incubation for 1 hour at room temperature the tubes are further incubated for 16-20 hours at 4° C. 1 ml of dextran-coated charcoal then added to the tubes which are further incubated on ice for 10 minutes. Following the incubation the samples are centrifuged at 10,000 g for 10 minutes and 500 ml of the supernatant added to 5 ml of scintillation cocktail. Measurement of the radio activity in the supernatant quantifies the amount of $[^3H]$-$TxB_2$ bound by the antibody. The concentration of unlabelled $TxB_2$ in the sample is then determined from a linear standard curve.

In the above mentioned test the representative compounds of Examples 3 and 4 gave $IC_{50}$ values of 115 and 72 μM respectively. In the same test the antihypertensive agent nifedipine had an $IC_{50} > 1000 \mu M$. $IC_{50}$ values represent the concentrations of drug which achieve 50% inhibition of $TxB_2$.

Some compounds of formula I have also oeen found to possess Phospholipase $A_2$ ($PLA_2$) inhibitory activity and hence are also indicated for use as antiinflammatory and antiallergic agents. Of partiCular interest for this activity are compounds of formula I wherein Ar represents an aryl radical havin9 a 2-nitro substituent For example the compound of Example 1 produced 90% inhioition of $PLA_2$ activity at a concentration of 100μM. $PLA_2$ activity was assayed by a procedure based on Franson, R. C., Chapter 12. Intracellular Metabolism of Ingested Phospholipids. Liposomes: from Physical Structure to Therapeutic Applications. North-Holland Biomedical Press, 1981, pp 349–380 and involving measuring the hydrolysis of E.coli membrane phospholipids and the release of free $[1-^{14}]$ oleic acid from the C-2 position of phospholipids by human platelet $PLA_2$.

Accordingly a second aspect of this invention provides a method for treating or preventing inflammatory or allergic conditions in a mammal which comprises administering to said mammal an effective amount of a compound of formula I wherein Ar is 2-nitrophenyl or a pharmaceutically acceptable salt thereof.

The compounds of formula I and intermeciates of analogous structure may be prepared by processes described in EP No. 100189.

The compounds of formula I may be conveniently prepared by a process comprising reacting corresponding compounds of formula

RCHO  (II)

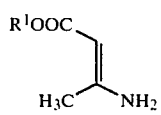

(III)

and

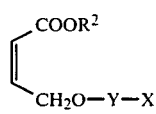

(IV)

wherein R, $R^1$, $R^2$, X and Y have the meanings above.

Another process for preparing compounds of formula I involves reacting ammonia with a compound of formula (V) and (VI):

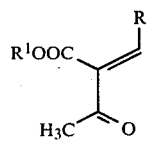

(V)

and

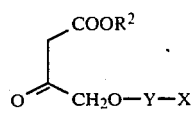

(VI)

wherein R, $R^1$, $R^2$, Y and X are as defined above.

The above mentioned processes are conveniently carried out by heating in an inert solvent such as ethanol.

When used in the method of this invention the compound of formula I, or a pharmaceutically acceptable acid addition salt thereof may be administered alone or in the form of a pharmaceutically acceptable composition. Suitable carriers are well known in the art. The particular dosage will depend on the chosen route of administration and standard pharmaceutical practice.

Preferably the composition is in unit dosage form, e.g. tablets or capsules.

Based on the experiments detailed hereinabove, the compounds of formula I or pharmaceutically acceptable salts thereof can be administered at a dose level of about 1 to 200 mg/day may be used for treating humans suffering from or at risk from thrombosis, atherosclerosis, peripheral vascular diseases, migraine or inflammatory or allergic conditions.

The following Examples illustrate the preparation of compounds of formula I:

EXAMPLE 1

1,4-Dihydro-2-methyl-4-(2-nitrophenyl)-6-[(3-pyridyl-methoxy)methyl]pyridine-3,5-dicarboxylic acid diethyl ester A mixture of ethyl 3-aminocrotonate (1.3g, 0.01 mol), ethyl 3-oxo-4-(3-pyridylmethoxy) butanoic acid (2.4 g 0.01 mol) and 2-nitrobenzaldehyde (1.56g, 0.01 m) in ethanol (50 ml) was refluxed for 23 hours. The solvent was removed under reduced pressure and the residue treated with diethyl ether and extracted with 2N hydrochloric acid. The separated aqueous phase was extracted with chloroform and the chloroform phase separated and evaporated. The residue was treated with acetone and left overnight. Solid material which separated was filtered off and discarded. The acetone solution was evaporated, treated with ammonia solution and extracted with chloroform ($\times 3$). The combined chloroform extracts were washed with water, dried ($MgSO_4$) and evaporated to give an oil. This was dissolved in ethyl acetate and treated with maleic acid (1 g). A little of the solvent was evaporated and acetone and diethyl ether added. The maleic salt of the title compound crystallised and was collected (2.6 g) mp 133–135° C.

Analysis:

$C_{25}H_{27}N_3O_7.C_4H_4O.\frac{1}{2}H_2O$ requires C, 57.42; H, 5.32; N, 6.93%;

Found: C, 57.42; H, 5.30; N, 6.83%.

EXAMPLE 2

1,4-Dihydro-2-methyl-4-(3-nitrophenyl)-6-[(3-pyridyl-methoxy)methyl]pyridine-3,5-dicarboxylic acid 5-ethyl-3-methyl diester Ethyl 3-nitrobenzylideneacetoacetate (2.5g, 0.01 and ethyl 3-oxo-4-(3-pyridylmethoxy)butanoic acid (3.0g) in ethanol (50 ml) with 0.88 ammonia (1 ml) was refluxed for 1 hour. The solvent was removed under reduced pressure and the residue treated with diethyl ether and 2N hydrochloric acid and separated. The aqueous acid solution was extracted with chloroform ($\times 3$). The combined chloroform extracts were evaporated and the residue treated with acetone and left to stand overnight. Crystalline solid was filtered off and discarded.

The acetone solution was evaporated and the residue dissolved in chloroform and washed with aqueous ammonia solution, dried ($MgSO_4$) and evaporated. The residue was dissolved in diethyl ether acidified with ethanolic HCl and a little ethyl acetate was added. The title compound crystallised as the hydrochloride salt and was collected by filtration and dried (1.74g) m.p. 139°–141° C.

Analysis:

$C_{24}H_{25}N_3O_7.HCl$ requires C, 57.20; N, 5.20; N, 8.34%;

Found: C, 57.50; H, 5.34; N, 8.54%

EXAMPLE 3

1,4-Dihydro-2-[(1-imidazolylethoxy)methyl]-6-methyl-4-(3-nitrophenyl)pyridine-3,5-dicarboxylic acid 3-ethyl 5-methyl diester Ethyl 3-nitrobenzylideneacetoacetate (5.0g 0.02 mol) and ethyl 3-oxo-4-(1-imidazolylethyloxy) butanoic acid (4.8 0.02 mol) in ethanol (50 ml) with 0.88 ammonia (4 ml) was refluxed for 7 hours. The solvent was removed under reduced pressure and the residue treated with diethyl ether and 2N hydrochloric acid and separated. The aqueous acid solution was extracted with chloroform ($\times 3$) then the combined organic extracts washed with dilute ammonia solution, dried ($MgSO_4$) and evaporated. The residue was purified by chromatography on silica using chloroform, to remove by-products, and then chloroform:methanol (9:1) to give the title compound.

Treatment of this product in ethyl acetate with ethanolic HCl gave the hydrochloride, hemihydrate of the title compound, mp 199°–201° C.

Analysis:

$C_{23}H_{26}N_4O_2.HCl\frac{1}{2}H_2O$ requires C, 53.54; H, 5.66; N, 10.86%;

Found: C, 53.48; H, 5.43; N, 10.97%.

EXAMPLE 4

1,4-Dihydro-2-methyl-4-(3-nitrophenyl)-6-[(3-pyridylethoxy)methyl] pyridine-3,5 dicarboxylic acid 5-ethyl-3-methyl diester Methyl 3-nitrobenzylidienacetoacetate (3.0g), ethyl 3-oxo-4-[2-(pyrid-3-yl)ethyloxy]butanoate (3.0g) and conc. ammonia (2 ml) in ethanol (50 ml) were refluxed for 6 hours. The solvent was removed under reduced pressure and the residue treated with ether and 2N hydrochloric acid, then separated. The aqueous acid phase was extracted with chloroform and the combined chloroform extracts washed with dilute ammonia solution, dried ($NaSO_4$) and evaporated.

The residue was purified by chromatography on silica using ethyl acetate as eluent to give the crude title compound (2.7 g). This was dissolved in ethyl acetate, treated with ethanolic HCl and evaporated to reduced volume. Treatment with ether gave the title compound as the hydrochloride hemihydrate, 2.0 g, m.p. 175°–177° C.

Analysis:

$C_{25}H_{27}N_3O_7.HCl,\frac{1}{2}H_2O$ requires: C, 56.98; H, 5.55; N, 7.97;

Found: C, 56.78; H, 5.08; N, 8.19%.

We claim:

1. A method for treating or preventing diseases responsive to inhibition of blood platelet aggregation or thromboxane synthetase in a mammal in need thereof which comprises administering to said mammal an amount effective to inhibit blood platelet aggregation or thromboxane synthetase of a compound of formula I

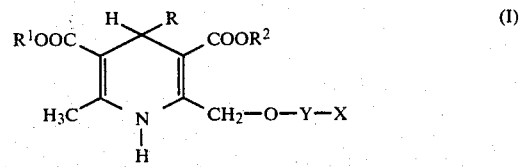

wherein

R is phenyl or optionally substituted phenyl;

$R^1$ and $R^2$ are each independently $C_1-C_4$ alkyl or 2-methoxyethyl;

Y is $—(CH_2)_n—, —CH_2CH(CH_3)—$ or $—CH_2C(CH_3)_2—$;

X is a 5 or 6 membered nitrogen containing aromatic heterocyclic ring optionally substituted by one or more $C_1-C_4$ alkyl, phenyl, benzyl, CN, $—N(R^3)_2$, $(CH_2)_mCO_2H$, $(CH_2)_mCO_2(C_1-C_4$ alkyl) or $(CH_2)_mCON(R^3)_2$ groups wherein each $R^3$ is independently H or $C_1-C_4$ alkyl and m is 0 or 1;

and n is 1 to 3 when X is linked by a ring carbon atom or 2 or 3 when X is linked by a ring nitrogen atom; and their pharmaceutically acceptable acid addition salts.

2. A method as claimed in claim 1 wherein X is an imidazolyl or pyridyl ring optionally substituted by 1 to 3 alkyl groups of 1 to 4 carbon atoms.

3. A method as claimed in claim 1 wherein X is 1-imidazolyl or 3-pyridyl.

4. A method as claimed in claim 1 wherein Y is —CH$_2$— or —CH$_2$CH$_2$—.

5. A method as claimed in claim 1 wherein R$^1$ and R$^2$ are each selected from methyl or ethyl.

6. A method as claimed in claim 1 wherein R is optionally substituted phenyl.

7. A method as claimed in claim 1 wherein R is 2- or 3- nitrophenyl; 2-chlorophenyl; 2,3-dichlorophenyl; 2-trifluoromethylphenyl or pentafluorophenyl.

8. A method for treating or preventing inflammatory or allergic conditions reponsive to inhibition of phosphilipase A$_2$ in a mammal in need thereof, which comprises adminstering to said mammal an amount effective to inhibit phosphilipase A$_2$ of a compound of formula Ia

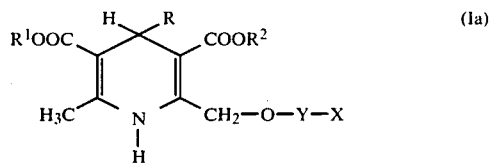

wherein
R is 2-nitrophenyl;
R$^1$ and R$^2$ are each independently C$_1$-C$_4$ alkyl or 2-methoxyethyl;
Y is —(CH$_2$)$_n$—, —CH$_2$CH(CH$_3$)— or —CH$_2$C(CH$_3$)$_2$—;
X is a 5 or 6 membered nitrogen containing aromatic heterocyclic ring optionally substituted by one or more C$_1$-C$_4$ alkyl, phenyl, benzyl, CN, —N(R$^3$)$_2$, (CH$_2$)$_m$CO$_2$H, (CH$_2$)$_m$CO$_2$H, (CH$_2$)$_m$CO$_2$(C$_1$-C$_4$ alkyl) or (CH$_2$)$_m$CON(R$^3$)$_2$ groups wherein each R$^3$ is independently H or C$_1$-C$_4$ alkyl and m is 0 or 1;
and
n is 1 to 3 when X is linked by a ring carbon atom or 2 or 3 when X is linked by a ring nitrogen atom; or a pharmaceutically acceptable acid addition salts thereof.

9. A method as claimed in claim 8 wherein R$^1$ and R$^2$ are independently methyl or ethyl.

10. A method as claimed in claim 8 wherein X is imidazolyl or pyridyl and Y is —CH$_2$— or —CH$_2$CH$_2$—.

11. A method as claimed in claim 8 wherein X is 1-imidazolyl or 3-pyridyl.

* * * * *